United States Patent [19]
Georgiade

[11] Patent Number: 5,219,360
[45] Date of Patent: Jun. 15, 1993

[54] MAMMARY PROSTHESIS FILL AND METHOD OF MAKING SAME

[75] Inventor: Nicholas G. Georgiade, Durham, N.C.

[73] Assignee: Fortis Research Corporation, Durham, N.C.

[21] Appl. No.: 698,302

[22] Filed: May 10, 1991

[51] Int. Cl.$^5$ .............................................. A61F 2/12
[52] U.S. Cl. .......................................... 623/8; 623/11
[58] Field of Search ................ 623/4, 6, 1, 11, 12, 623/13, 15, 17, 16, 66, 8

[56] References Cited

U.S. PATENT DOCUMENTS

| | | | |
|---|---|---|---|
| 4,141,973 | 2/1979 | Balazs | 424/180 |
| 4,500,676 | 2/1985 | Balazs et al. | 525/542 |
| 4,582,865 | 4/1986 | Balazs et al. | 524/29 |
| 4,605,691 | 8/1986 | Balazs et al. | 524/27 |
| 4,636,524 | 1/1987 | Balazs et al. | 514/781 |
| 4,713,072 | 12/1987 | Bowald | 623/6 |
| 4,713,448 | 12/1987 | Balazs et al. | 536/55.1 |
| 4,731,081 | 3/1988 | Tiffany | 623/8 |
| 4,888,016 | 12/1989 | Langerman | 623/4 |
| 4,904,260 | 2/1990 | Ray et al. | 623/17 |

OTHER PUBLICATIONS

Weiss et al., The Role of Na-Hylan in Reducing Post-surgical Tendon Adhesions; Bull. Hosp. J. Dis. Ortho. Inst. 46:9-15 (1986).
Balazs et al., Hyaluronan, Its Crosslinked Derivative—Hylan—and Their Medical Applications, Proc. Int. Conf. Cellulosics Util. (1988).
Balazs et al., Hylan: Hyaluronan Derivatives for Soft Tissue Repair and Augmentation, Proc. Fifth, Inc. Conf. on Biotech. (1988).
Balazs et al., Clinical Uses of Hyaluronan, CIBA Foundation Symposium #143 (1988).
McCain et al., Preliminary Studies on the Use of a Viscoelastic Solution in Arthroscopic Surgery of the Temporomandibular Joint, J. Oral Maxillofac. Surg. 58:24 (1989).

*Primary Examiner*—David Isabella
*Attorney, Agent, or Firm*—Olive & Olive PA

[57] ABSTRACT

A surgical mammary prosthesis containing a liquid-gel of cross-linked hyaluronic acid (hylan) inside a medical grade elastomer, and a method of making a prosthesis containing such a liquid-gel. Because the gel used in the invention contains a nontoxic, nonantigenic, noninflammatory, biodegradable natural substance, problems attributed to or associated with previous silicone gel filled prostheses as a result of prosthesis rupture or leakage or "bleed" are avoided.

8 Claims, 2 Drawing Sheets

MAMMARY PROSTHESIS FILL AND METHOD OF MAKING SAME

BACKGROUND OF THE INVENTION

1. Field of the Invention

This invention relates to surgically implanted mammary prostheses, and in particular pertains to an inflating liquid-gel for mammary prostheses.

2. Description of the Related Art

Mammary prostheses which are implanted surgically generally are made of a silicone medical grade elastomer shell. The prostheses may have added texture to aid in adhesive bonding of the surgically inserted prosthesis to the body tissue. The shell comprises multiple layers of silicone coating and may include an elastomer barrier coat surrounded by the silicone elastomer layer to minimize leakage of inner silicone gel. Mammary prostheses may rupture, both as the result of accidents and when the surrounding shell develops a crease. Such a rupture may be a problem because the integrity and form of the prosthesis is destroyed. Also, the body tissues are exposed to the silicone gel when the prosthesis ruptures.

Attempts to eliminate the problem of leakage of the silicone have included development of more durable shell materials and structures. Tiffany et al. developed a uniformly dispersed lubricating material in saline to reduce the tendency of the shell to crease with resultant failure of the shell (U.S. Pat. No. 4,731,081). The disclosure of this patent and all other patents and publications cited herein is incorporated herein by reference.

The lubricating substance of Tiffany et al. is a solution or suspension of hydrophilic polymer material such as polyvinylpyrrolidone, polyvinyl alcohol, hydroxyethl starch and lecithin, wetting agents such as fatty acid salts or esters, or cottonseed oil or peanut oil. The concentration of the lubricating agent is less than 70% and preferably 5-10% by weight in saline.

Other problems with mammary prostheses include problems with the healing at the surface of the prosthesis. Alterations in texture and addition of surface coverings, such as polyurethane, have not solved the problem, and the latter are believed to cause problem due to toxic or carcinogenic effects.

Applicant herein uses a non-silicone liquid-gel consisting of cross-linked hyaluronan, also recognized as cross-linked hyaluronic acid and hylan (HA,HY). By the term "liquid-gel" herein, Applicant includes viscous liquids or gels of the cross-linked substance. The consistency which is desired determines whether a viscous liquid or a gel of hylan is used in the prosthesis of the invention. Hyaluronic acid (not cross-linked) is a polysaccharide which occurs naturally in chicken combs, vitreous, synovial fluid, skin and human umbilical cords. It is a glycosaminoglycan containing repeating disaccharide units of N-acetyl-D-glucosamine and D-glucuronic acid, the monosaccharide units being linked together with beta 1-4 bonds and disaccharide units being linked with beta 1-3 glycoside bonds to form an unbranched, uncrosslinked polysaccharide chain. Hyaluronic acid generally is found as the sodium salt. HA has been found to promote would healing and to minimize scar formation.

To obtain relatively pure HA, animal connective tissue may be extracted with chloroform-water (U.S. Pat. No. 4,141,973 of Balazs). A 10% NaCl solution of the extract is chloroform extracted. The aqueous phase is adjusted to pH 4-5, followed by another chloroform extraction and/or enzyme treatment. The pH of the new aqueous phase is adjusted to 6-7 followed by another chloroform extraction or high speed centrifugation and complete mixing. The new aqueous phase is filter sterilized and then the HA is ethanol and then acetone precipitated. The resultant HA fraction is sterile, pyrogen free, essentially free of proteins, peptides and nucleic acid impurities, non-antigenic, high molecular weight and does not cause an inflammatory reaction.

A number of bacteria, such as *Streptococcus pyogenes, Staphylococcus aureus,* and *Clostridium perfringens*, produce hyaluronidases. Bacterial hyaluronidases may be used to extract hyaluronic acid from sources such as tissue.

Elastoviscous solutions of highly purified HA have been used in ophthalmological viscosurgery and in viscosupplementation of joint fluid using elastoviscous hyaluronan solutions, for example, in the treatment of equine traumatic arthritis.

Hyaluronic acid can be extracted from sources such as animal tissue. It can be chemically modified in situ before it is extracted from animal tissue, by treatment of the tissue with a substance which reacts with proteins such as formaldehyde, glutaraldehyde or glyoxal (U.S. Pat. No. 4,713,448 of Balazs et al.). Such a treatment produces a water extract of a modified HA, termed "Hylan" (HY) with a substantially lower protein content per cubic centimeter than in the absence of the treatment. HY can have a very high weight-average molecular weight of $13 \times 10^8$ or less. A polymer of any desired molecular weight can be obtained by exposure of the HY to compounds or other agent capable of breaking the glucosidic bonds such as hyaluronidase.

In solutions of 0.5% and higher, HY differs significantly from uncrosslinked HA in its physico-chemical and rheological characteristics, which appears to be due to major changes in macromolecular structure, including additional covalent crosslinks introduced during the treatment with a protein crosslinking immobilizing agent as discussed in the '448 patent. The HY modified structure is sufficient to greatly increase the elastic characteristics of solutions of the HY, without any adverse effect on the beneficial HA characteristics, to provide very viscous aqueous solutions, and to allow it to retain its biocompatibility.

The HY may also be treated with divinyl sulfone (DVS) to provide a highly viscous solution in 0.15M NaCl with only 0.15 to 0.40 wt %. This viscosity decreases with shear rate. The HY also has a very long relaxation time. DVS reacts with HA or its salts in aqueous alkaline solutions to form cross-linked gels (U.S. Pat. No. 4,605,691 of Balazs et al.). The gels swell in aqueous environments, with the swelling being dependent on the degree of cross-linking, which can be controlled by changing the HA molecular weight or concentration, the alkali concentration or the HA/DVS ratio. See also U.S. Pat. Nos. 4,582,865 and 4,636,524 of Balazs et al.

Cross-linked forms of hyaluronans, called hylans, may be formed into water-insoluble soft gels for use as viscosurgical implants in the prevention of postoperative adhesions and scar formation. The use of hylan devices is discussed in Balazs et al. (CIBA Foundation Symposium #143, The Biology of Hyaluronan, John Wiley and Sons, Chichester, Sussex, 1988).

For example, hylan gels are effective in diminishing adhesion formation between the tendon and tendon sheath in the toe; in protecting articular cartilage from scuffs during surgery; in facilitating control of tissue movements, visualization during surgery and collection of blood and tissue debris in surgery; and in arthroscopic surgery of the temporomandibular joint (J. Oral Maxillofac. Surg. 47:(161,1989).

It is therefore an object of this invention to provide a mammary prosthesis containing a gel of a biocompatible, non-toxic, non-immunogenic, and non-inflammatory cross-linked HA in an approximately 99% saline solution.

It is a further object of this invention to provide a method of making such a prosthesis.

Other objects and advantages will be more fully apparent from the following disclosure and appended claims.

SUMMARY OF THE INVENTION

The invention comprises a surgically implantable mammary prosthesis, with or without a textured exterior, containing chemically modified hyaluronic acid (HA), a natural polysaccharide, with crosslinking of the HA chains in molecular structures called hylans. The exterior surface may also be coated with hylan or the uncrosslinked hyaluronic acid.

Overall, the hylans, which have a molecular weight of about 8-23 million, have varying elastomeric capabilities when prepared as a water insoluble gel or saline composition and thus can be formulated to a desired consistency by those of skill in the art. Body tissues do not react with these gels as foreign bodies, because the hylans are biocompatable, and nontoxic and do not cause an inflammatory response. The small amount of protein in hylan (0.4-0.8%) is hidden between two or more HA chains and therefore not capable of being antigenic. The water content of the hylan gel is about 99.3 to 99.7% and preferably is in the form of water or physiological saline.

In the invention, a cross-linked hylan liquid-gel is used to fill the elastomer envelope of a mammary prosthesis completely and then the envelope is sealed with an appropriate plug and adhesive.

Other aspects and features of the invention will be more fully apparent from the following disclosure and appended claims.

DETAILED DESCRIPTION OF THE INVENTION AND PREFERRED EMBODIMENTS THEREOF

The present invention includes a mammary prothesis, comprising:
(a) a flexible envelope with or without a textured outer surface, said envelope having an inner space;
(b) a means of filling the envelope inner space with a liquid or gel; and
(c) a crosslinked hyaluronic acid liquid (hylan)-gel positioned within said inner space.

Figure 1:
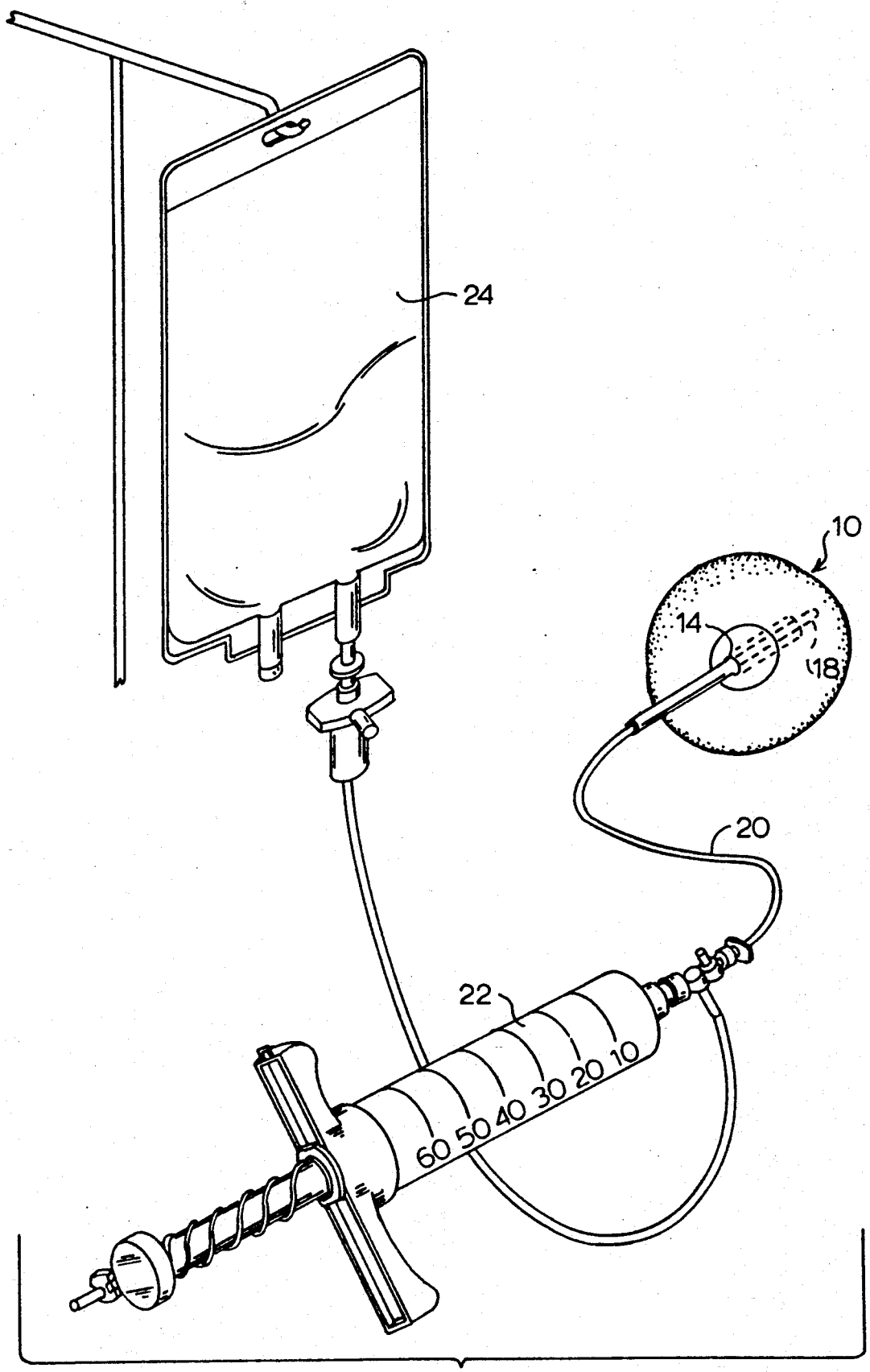
FIG. 1 is a perspective view of a prosthesis and an apparatus for filling the prosthesis

FIG. 1 shows an example of an arrangement for filling a prosthesis 10 with a liquid-gel 16 according to the invention.

Figure 2:
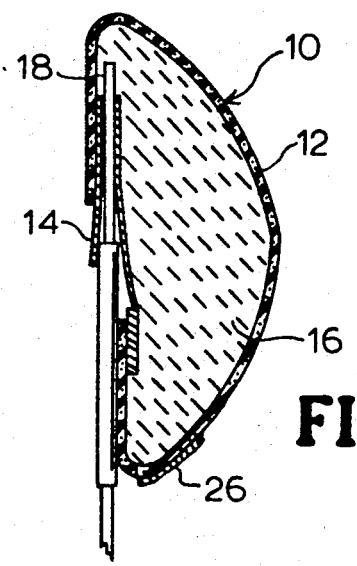
FIG. 2 is a cross-sectional view of an implantable mammary prosthesis which may be used in the invention showing insertion of a needle for filling the prosthesis.

FIG. 2 shows a cross-sectional view of a mammary prosthesis 10 which may be used in the invention. The prosthesis 10 as shown includes a flexible shell or envelope 12, a filling valve 14 and an inflating liquid-gel 16.

In one preferred method of filling the prosthesis 10, a needle 18 is connected by tubing 20 to a syringe 22. The syringe 22 is filled from a reservoir 24 of liquid-gel material and the syringe-full of material is injected into the prosthesis 10. For a standard size prosthesis, a 60-cc syringe may be filled and emptied about five times to fill the prosthesis.

The inflating liquid-gel 16 of the invention is a cross-linked, hyaluronic acid derived compound. Preferably, the consistency of the liquid-gel is approximately the same as the breast tissue and consistent with prior inorganic inflating liquid-gels. Adjusting the consistency of cross-linked HA to a desired consistency may be easily done and is known in the art. For example, as discussed in Balazs et al., (U.S. Pat. No. 4,582,865), by varying the concentration of NaCl in which gel particles are placed from 0.05M to 1.00M, variations in swelling ratio from 176 to 990 may be obtained. The greater the swelling, the softer is the liquid-gel.

The cross-linking of the HA for use in the invention is preferably accomplished through divinyl sulfone treatment of HA (U.S. Pat. Nos. 4,582,865; 4,605,691; and 4,636,524 of Balazs et al.) or via bacterial metabolism of HA, which has been or may be treated to have aldehyde cross-linking groups covalently bonded to the HA as taught by Balazs et al. (U.S. Pat. No. 4,713,448). Alternatively, other cross-linked hyaluronic acid liquid-gels may be used for the inflating liquid as are known in the art of making such gels.

A deflated envelope 12 for use in the invention may be surgically implanted into a breast through a surgical opening, and the crosslinked HA inflating liquid-gel 16 may be added to the envelope 12 by means of a syringe or other inflating device as discussed above or as otherwise known in the art.

Alternatively, the crosslinked HA inflating liquid-gel 16 may be added to a flexible envelope 12 and sealed into the flexible envelope 12 prior to insertion by the mammary prosthesis manufacturer or later using known methods for filling and sealing. The prosthesis 10 may then be surgically implanted through a surgical opening in the breast which is then closed by means known in the art.

It is understood that the type of prosthesis envelope 12 used and the manner of filling the prosthesis envelope 12 with the inflating liquid-gel 16, may be chosen from any as are known in the art.

It is known in the art to texture prostheses or to coat prosthesis to minimize scar contracture. In one embodiment, the envelope 12 used in the invention is coated with a layer 26 of additional hylan. Alternatively, natural (uncross-linked) hyaluronic acid may be used as an external coating on the envelope.

The features and advantages of the present invention will be more clearly understood by reference to the following examples, which are not to be construed as limiting the invention.

EXAMPLES

Example 1

This example illustrates extraction of modified sodium hyaluronate from rooster combs as is also disclosed in U.S. Pat. No. 4,713,448. Rooster combs are washed with a 1% aqueous cetylpyridinium chloride solution and then deionized water, and are frozen. Frozen comb slices (1-2 mm thick) are placed in a mixture of an equal weight of acetone, 100 g 37% formalin and 50 g sodium acetate, with stirring for 24 hours at about 20° C. After filtration the comb slices are washed in acetone and air dried to about half their original weight. After water extraction (5 volumes water) for 72 hours, the comb slices are filtered from the extract. The extract is precipitated with 2 volumes acetone and sodium acetate (10 g/l extract) and the precipitate washed with acetone and vacuum dried.

Alternatively to formalin and sodium acetate glutaraldehyde; glyoxal in water; isopropanol formalin/sodium acetate/chloroform or the like as disclosed in U.S. Pat. No. 4,713,448, are used to extract modified HA from rooster combs.

Example 2

This example illustrates a method of obtaining a gel from the HA. An aliquot of a precipitated HA from Example 1 is mixed in an approximate ratio of 0.03:1 by weight with 0.05N NaOH in water, and stirred to form a viscous solution. A 0.26:1 mixture of divinyl sulfone and aqueous 0.5N NaOH is added in a ratio of about 0.04:1 to the viscous solution, stirred for 10 minutes and left 50 minutes at room temperature to form an elastic, colorless, clear gel. Saline solution (0.15M) is added to swell the gel and form clear jelly-like substance with a concentration of about 0.275% HA as found in Balazs et al. (U.S. Pat. No. 4,713,448).

Example 3

This example illustrates addition of hylan liquid-gel such as that of Example 2 to a prosthetic envelope. A prosthesis is used which comprises a high performance medical grade elastomer with or without a laminated interspersed layer of an elastomer barrier coat such as is made by Dow Corning Corporation (Midland, Mich.). Alternatively, a prosthetic envelope made by McGhan Medical Corporation (Santa Barbara, Calif.), Mentor Corporation (Goleta, Calif.), Heyer-Schulte Corporation (Goleta, Calif.), or another prosthesis known in the art may be used.

The gel is added to the envelope via a syringe of the appropriate size and strength and injected directly into the deflated envelope via a 20 plus gauge needle or its equivalent. If the filling is carried out by the manufacturer, the filling is carried out by the manufacturer, the filling is carried out through a small prepared opening in the base of the prosthesis, which is subsequently sealed using standard techniques of mammary prosthesis manufacturers.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An implantable mammary prosthesis to augment natural breast tissue comprising:
   (a) a hollow shell formed of a flexible elastomeric envelope, said shell having an inner volume and an exterior surface, said prosthesis adapted to be surgically implanted in a human breast so that the envelope retains a desired shape when said inner volume is filled by a liquid-gel substance;
   (b) said envelope having a means for filling the envelope inner volume with said liquid-gel; and
   (c) said liquid-gel filling said inner volume is a cross-linked hyaluronic acid.

2. A mammary prosthesis according to claim 1, wherein the hyaluronic acid liquid-gel has aldehyde cross-linking groups.

3. A mammary prosthesis according to claim 1, further comprising hyaluronan placed on the exterior surface of the envelope.

4. An implantable mammary prosthesis to augment natural breast tissue, said prosthesis having a a hollow shell formed of a medical grade elastomer, said hollow shell having an outer layer and inner volume filled with a liquid-gel, said prosthesis adapted to be surgically implanted in a human breast so that the shell retains a desired shape when said inner volume is filled with a liquid-gel said liquid-gel filling said inner volume is cross-linked hyaluronan.

5. A method of making a surgically implantable mammary prosthesis to augment natural breast tissue, comprising:
   (a) providing a hollow shell formed of a flexible elastomeric envelope defining an inner volume and said envelope having a means for filling said inner volume, said prosthesis adapted to be surgically implanted in a human breast so that the envelope retains a desired shape when said hollow shell is filled by a liquid-gel substance; and
   (b) filling said inner volume through said filling means with said liquid-gel wherein said liquid-gel is cross-linked hyaluronic acid.

6. A method according to claim 5, wherein the hyaluronic acid liquid-gel comprises hyaluronan with aldehyde cross-linking groups.

7. A method according to claim 5, wherein said cross-linked hyaluronic acid liquid gel is formed by obtaining hyaluronic acid from rooster combs, and treating said hyaluronic acid to have aldehyde cross-linking groups covalently bonded to the hyaluronic acid.

8. A method according to claim 7, wherein said cross-linked hyaluronic acid is formed from hyaluronic acid reacted with divinyl sulfone.

* * * * *

UNITED STATES PATENT AND TRADEMARK OFFICE
CERTIFICATE OF CORRECTION

PATENT NO. : 5,219,360

DATED : June 15, 1993

INVENTOR(S) : Nicholas G. Georgiade

It is certified that error appears in the above-identified patent and that said Letters Patent is hereby corrected as shown below:

Column 2, line 31: replace "$10^8$" by --$10^6$--.

Signed and Sealed this

Fifth Day of July, 1994

Attest:

BRUCE LEHMAN

*Attesting Officer*  *Commissioner of Patents and Trademarks*